US006551970B2

(12) United States Patent
Decoster et al.

(10) Patent No.: US 6,551,970 B2
(45) Date of Patent: Apr. 22, 2003

(54) DETERGENT COSMETIC COMPOSITIONS FOR HAIR-CARE APPLICATION AND USE THEREOF

(75) Inventors: Sandrine Decoster, Epinay-sur-Seine (FR); Bernard Beauquey, Clichy (FR)

(73) Assignee: L'Oréal, Paris (FR)

(*) Notice: Subject to any disclaimer, the term of this patent is extended or adjusted under 35 U.S.C. 154(b) by 0 days.

(21) Appl. No.: 10/058,796

(22) Filed: Jan. 30, 2002

(65) Prior Publication Data

US 2002/0147120 A1 Oct. 10, 2002

Related U.S. Application Data

(63) Continuation of application No. 09/180,326, filed as application No. PCT/FR97/00686 on Nov. 5, 1998, now abandoned.

(30) Foreign Application Priority Data

May 6, 1996 (FR) .............................................. 96 05643

(51) Int. Cl.$^7$ .......................... A61K 7/075; A61K 7/50; C11D 1/94; C11D 3/37
(52) U.S. Cl. ....................... 510/122; 510/119; 510/121; 510/123; 510/124; 510/125; 510/127; 510/129; 510/159; 510/405; 510/426; 510/433; 510/466; 510/481; 510/493; 510/504; 134/42; 424/70.5; 424/70.12; 424/70.122; 424/70.19; 424/70.21; 424/70.22; 424/70.24; 424/70.28
(58) Field of Search .................. 510/119, 121–125, 510/127, 129, 159, 405, 426, 433, 466, 481, 493, 504; 134/42; 424/70.5, 70.12, 70.122, 70.19, 70.21, 70.22, 70.24, 70.28

(56) References Cited

U.S. PATENT DOCUMENTS

| | | | |
|---|---|---|---|
| 3,589,578 A | 6/1971 | Kamphausen | 226/40 |
| 4,031,307 A | 6/1977 | DeMartino et al. | 536/114 |
| 4,954,335 A | 9/1990 | Janchiraponvei | 424/70 |
| 5,152,914 A | 10/1992 | Forster et al. | 252/174 |
| 5,275,755 A | 1/1994 | Sebag et al. | 252/174.15 |
| 5,308,551 A | 5/1994 | Beauquey et al. | 252/548 |
| 5,439,682 A | 8/1995 | Wivell et al. | 724/401 |
| 5,536,493 A | 7/1996 | Dubief | 424/70.13 |
| 5,543,074 A | 8/1996 | Hague et al. | 510/122 |
| 5,560,918 A | 10/1996 | Wivell et al. | 424/401 |
| 5,599,549 A | 2/1997 | Wivell et al. | 424/401 |
| 5,720,961 A | 2/1998 | Flower et al. | 424/401 |
| 5,776,872 A | 7/1998 | Giret et al. | 510/124 |
| 5,876,705 A | 3/1999 | Uchiyama et al. | 424/70.12 |
| 5,883,058 A | 3/1999 | Wells et al. | 510/127 |
| 6,106,816 A | 8/2000 | Hitchen | 424/70.16 |

FOREIGN PATENT DOCUMENTS

| | | | | |
|---|---|---|---|---|
| EP | 0 181 773 | | 5/1986 | |
| EP | 0 400 976 | | 12/1990 | |
| EP | 0 413 417 | | 2/1991 | |
| EP | 0 432 951 B1 | | 6/1991 | |
| EP | 0 463 780 | | 1/1992 | |
| EP | 0 468 721 | | 1/1992 | |
| EP | 0 530 974 | | 3/1993 | |
| EP | WO 93/08787 | * | 5/1993 | ............ A61K/7/06 |
| EP | 0 522 024 | | 7/1993 | |
| WO | WO 92/10162 | | 6/1992 | |
| WO | WO 94/03152 | | 2/1994 | |
| WO | WO 96/19188 | | 6/1996 | |
| WO | WO 97/35549 | | 10/1997 | |

* cited by examiner

Primary Examiner—Mark Kopec
Assistant Examiner—Brian P. Mruk
(74) Attorney, Agent, or Firm—Finnegan, Henderson, Farabow, Garrett & Dunner, LLP

(57) ABSTRACT

The invention relates to new detergent and conditioning hair-care compositions comprising (A) a washing base comprising an anionic surfactant and an amphoteric $C_{10}$–$C_{14}$ alkylbetaine surfactant, (B) a conditioning system comprising at least one cationic guar gum and at least one insoluble silicone, the silicone being introduced into the composition in non-emulsified form, and (C) a cosmetically acceptable medium, as well as a process of cleansing and conditioning the hair by application of the composition.

23 Claims, No Drawings

DETERGENT COSMETIC COMPOSITIONS FOR HAIR-CARE APPLICATION AND USE THEREOF

This is a continuation of application Ser. No. 09/180,326, filed Nov. 5, 1998, which is a National Stage Entry of Application No. PCT/FR97/00686, and which was refiled on Aug. 9, 2000, as a Continued Prosecution Application, which are incorporated herein by reference.

The present invention relates to new cosmetic compositions having improved properties, intended simultaneously for cleansing and conditioning the hair, and comprising, in a cosmetically acceptable vehicle, a washing base consisting of particular surfactants having detergent power, in which base are also present, as conditioning agents, particular cationic polymers in combination with particular insoluble silicones. The invention also relates to the use of the said compositions in the abovementioned cosmetic application.

For cleansing and washing the hair, the use of detergent hair-care compositions (or shampoos) based essentially on traditional surfactants, in particular of the anioic, nonionic and/or amphoteric type, but more especially of the anionic type, is common. These compositions are applied to wet hair, and the lather generated by massage or friction with the hands makes it possible, after rinsing with water, to remove the various kinds of soil initially present on the hair.

These base compositions admittedly possess good washing power, but the intrinsic cosmetic properties which are associated with them remain, however, rather poor, in particular on account of the fact that the relatively aggressive nature of such a cleansing treatment can lead eventually, on the hair fibre, to more or less pronounced damage, linked especially to the progressive removal of the lipids or proteins contained in or at the surface of the fibre.

Thus, in order to improve the cosmetic properties of the above detergent compositions, and more especially of those which are required for application to sensitized hair (i.e. hair which is damaged or weakened, in particular through the chemical action of environmental agents and/or of hair treatments such as permanent-waving, dyeing or bleaching), it is now usual to introduce into these compositions supplementary cosmetic agents termed conditioning agents, intended mainly to rectify or limit the harmful or undesirable effects induced by the various treatments or types of attack to which the hair fibres are subjected more or less repeatedly. These conditioning agents can, of course, also improve the cosmetic behaviour of natural hair.

The conditioning agents most commonly used to date in shampoos are cationic polymers, silicones and/or silicone derivatives which, in effect, impart to the washed, dry or wet hair an ease of disentangling, softness and a smoothness which are markedly enhanced in comparison to what can be obtained with the corresponding cleansing compositions which do not contain them.

On sensitized hair, in order to obtain the cosmetic effects of silicones over the entire length of the hair fibre, it is preferable to use combinations of silicones and cationic polymers.

However, and in spite of the progress recently made in the field of shampoos based on cationic polymers and silicones, these latter do not really prove completely satisfactory, so that there is still at the present time a strong need to be able to have at one's disposal new products displaying improved performance in respect of one or more of the cosmetic properties mentioned above.

The present invention is directed towards meeting this need.

Thus, following a considerable amount of research conducted on this topic, it has now been found by the Applicant, completely unexpectedly and surprisingly, that, by using a particular washing base, namely a washing base combining at least one anionic type surfactant and at least one amphoteric surfactant of the $C_{10}$–$C_{14}$ alkylbetaine type, simultaneously comprising, in addition, particular, appropriately selected silicones as are defined below, and particular cationic polymers, namely guar gums, as conditioning agents, it is possible to obtain detergent compositions displaying excellent cosmetic properties, especially in respect of the ease of styling, the hold, the liveliness, the smoothness and the suppleness of the treated hair, as well as very good intrinsic washing power.

While there is no wish to limit the present invention to a theory of any kind, there would appear to exist, between the cationic polymer, the silicone, the anionic surfactant and the amphoteric surfactant, which are according to the invention, and the hair, particular affinities and/or interactions which favour an even, substantial and lasting deposition of the said silicone and/or the said cationic polymer at the surface of the said hair, this qualitative and quantitative deposition probably being one of the causes of the observed improvement in respect of the final cosmetic properties, especially the ease of disentangling of the wet or dried hair, the ease of styling and the smoothness from the root to the end of the treated hair. Be that as it may, the cosmetic properties associated with the compositions comprising an anionic surfactant, an amphoteric surfactant of the alkylbetaine type and the combination of conditioning agents [cationic guar gum/specific silicone] according to the invention are markedly superior to those which can be obtained employing compositions not comprising the simultaneous presence of all these essential compounds.

All these discoveries underlie the present invention.

Thus, according to the present invention, provision is now made for new detergent and conditioning hair-case compositions comprising, in a cosmetically acceptable medium, (A) a washing base comprising at least one anionic surfactant and at least one amphoteric surfactant of the $C_{10}$–$C_{14}$ alkylbetaine type, and (B) a conditioning system comprising at least one cationic guar gum and at least one insoluble silicone of viscosity less than or equal to 350 Pa.s (350,000 cSt), chosen from:

(i) polydialkylsiloxanes, (ii) polydiarylsiloxanes and (iii) polyalkylarylsiloxanes, the said silicone being introduced into the composition in non-emulsified form.

The subject of the invention is also the use in cosmetics of the above compositions for cleansing and conditioning the hair.

However, other characteristics, aspects and advantages of the invention will become still more clearly apparent on reading the description which follows, as well as the specific but in no way limiting examples designed to illustrate it.

As stated above, the essential constituents participating in the composition of the hair-case products of the invention are (A) a washing base comprising at least one anionic detergent surfactant and (ii) at least one amphoteric surfactant of the $C_{10}$–$C_{14}$ alkylbetaine type and (B) a conditioning system comprising (i) the cationic guar gum or gums and (ii) the insoluble silicone or silicones.

A—WASHING BASE:

The compositions according to the invention necessarily comprise a washing base, which is generally aqueous.

The surfactant or surfactants forming the washing base comprise one or more anionic surfactants and one or more amphoteric $C_{10}$–$C_{14}$ alkylbetaine surfactants.

The minimum amount of washing base is that which is just sufficient to impart a satisfactory lathering and/or detergent power to the final composition, and excessively large amounts of washing base do not really provide any additional advantages.

Thus, according to the invention, the washing base can represent from 4% to 50% by weight, preferably from 10% to 35% by weight and still more preferably from 12% to 25% by weight of the total weight of the final composition.

According to a preferred characteristic of the hair-care compositions according to the present invention, the washing base does not contain surfactants other than anionic surfactants and amphoteric surfactants of the $C_{10}$–$C_{14}$ alkylbetaine type.

(i) Anionic surfactant(s):

In the context of the present invention, the nature of these does not actually assume critical importance.

Thus, as an example of anionic surfactants which can be used, alone or mixed, in the context of the present invention, there may be mentioned, in particular (non-limiting list), the salts (especially alkali metal salts, in particular sodium salts, ammonium salts, amine salts, salts of amino alcohols or magnesium salts) of the following compounds: alkyl sulphates, alkyl ether sulphates, alkylamido ether sulphates, alkylaryl polyether sulphates, monoglyceride sulphates, alkylsulphonates, alkyl phosphates, alkylamidesulphonates, alkylarylsulphonates, α-olefin sulphonates, paraffin sulphonates; alkylsulphosuccinates, alkyl ether sulphosuccinates, alkylamidesulphosuccinates; alkylsulphosuccinamates; alkylsulphoacetates; alkyl ether phosphates; acylsarcosinates; acylisethionates and N-acyltaurates; the alkyl or acyl radicals of all these different compounds preferably containing from 12 to 20 carbon atoms, and the aryl radical preferably denoting a phenyl or benzyl group. Among anionic surfactants which can also be used, there may also be mentioned fatty acid salts such as the salts of oleic, ricinoleic, palmitic and stearic acids, and coconut oil or hydrogenated coconut oil acids; and acyllactylates in which the acyl radical contains 8 to 20 carbon atoms. It is also possible to use weakly anionic surfactants, such as alkyl D-galactosiduronic acids and their salts, as well as polyoxyalkylenated ether carboxylic acids and their salts, especially those containing from 2 to 50 ethylene oxide groups, and mixtures thereof. The anionic surfactants of the type comprising polyoxyalkylenated ether carboxylic acids or salts are, in particular, those which correspond to the following formula (I):

(1)

in which:

$R_1$ denotes an alkyl or alkylaryl group and n is an integer or decimal number (average value) which can vary from 2 to 24 and preferably from 3 to 10, the alkyl radical having between 6 and 20 carbon atoms approximately, and aryl preferably denoting phenyl, A denotes H, ammonium, Na, K, Li, Mg or a monoethanolamine or triethanolamine residue. It is also possible to use mixtures of compounds of formula (I), especially mixtures in which the groups $R_1$ are different.

Among all these anionic surfactants, it is preferable to use, more especially, the salts of alkyl sulphates and of alkyl ether sulphates, as well as mixtures thereof.

(ii) Amphoteric surfactant(s):

According to the invention, the amphoteric surfactants have to be chosen from the ($C_{10}$–$C_{14}$)alkylbetaines of formula:

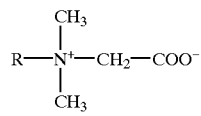

in which R denotes a linear or branched $C_{10}$–$C_{14}$, and preferably $C_{12}$–$C_{14}$, alkyl radical.

In particular, it is preferable to use the cocoylbetaine sold by the company HENKEL under the name DEHYTON AB 30.

B—CONDITIONING SYSTEM (i) Cationic guar gum(s):

The compositions according to the invention necessarily comprise, in addition, a cationic guar gum.

Generally speaking, for the purposes of the present invention, the term "cation guar gum" is understood to mean any guar gum containing cationic groups and/or groups which can be ionized to cationic groups.

Preferred cationic groups are chosen from those containing primary, secondary, tertiary and/or quaternary amine groups.

The cationic guar gums used generally have a weight-average molecular mass of between 500 and $5 \times 10^6$ approximately, and preferably between $10^3$ and $3 \times 10^6$ approximately.

The cationic guar gums which can be used according to the present invention are, for example, guar gums containing trialkylammonium cationic groups. Preferably, 2 to 30%, in numerical terms, of the hydroxyl functions of these guar gums bear trialkylammonium cationic groups.

Among these trialkylammonium groups, trimethylammonium and triethylammonium groups may be mentioned most especially.

Still more preferably, these groups represent from 5 to 20% by weight of the total weight of the modified guar gum.

According to the invention, it is preferable to use a guar gum modified with 14 hydroxypropyltrimethylammonium groups.

These guar gums modified with cationic groups are products which are already known per se, and are, for example, described in U.S. Pat. Nos. 3,589,578 and 4,031,307. Such products are, moreover, sold, in particular, under the trade names JAGUAR C13 S, JAGUAR C 15, JAGUAR C 17 and JAGUAR C162 by the company MEYHALL.

According to a preferred characteristic of the hair-care compositions according to the invention, these compositions do not contain cationic polymers other than cationic guar gums.

(ii) Silicone(s):

According to an essential characteristic of the detergent hair-care compositions according to the invention, these compositions contain, in addition, at last one specific insoluble silicone. Furthermore, this silicone must not have been introduced into the compositions in emulsion form.

According to the present invention, the term insoluble is understood to mean insoluble in the final composition.

The viscosity of these insoluble silicones is preferable between 1,000 and 350,000 cSt and more especially between 10,000 and 200,000 cSt (between 20 and 200 Pa.s), and still more preferably between 30,000 and 100,000cSt.

The viscosity of these silicones is measured at 25° C. according to ASTM Standard 445 Appendix C.

This silicone is chosen from (i) polydialkylsiloxanes, (ii) polydiarylsiloxanes and (iii) polyalkylarylsiloxanes, The alkyl radicals contain, in particular, from 1 to 10 carbon atoms, and especially denote methyl. The aryl radicals more especially denote phenyl.

Among polydialkylsiloxanes, there may be mentioned mainly:

polydimethylsiloxanes containing terminal trimethylsilyl groups, such as, for example, and without implied limitation, the SILBIONE oils of 70047 series, marked by RHONE POULENC, or some VISCASIL products from GENERAL ELECTRIC (Viscosil 60,000), the FLUID DC 200 products from the company DOW CORNING or the silicone oil AK 300,000 from the company WACKER;

polydimethylsiloxanes containing terminal hydroxydimethylsilyl groups, such as the oils of the 48 V series from RHONE POULENC or the product Q2-1401 marketed by the company DOW CORNING.

In this class of polydialkylsiloxanes, there may also be mentioned the polydialkylsiloxanes sold by the company GOLDSCHMIDT under the trade names ABILWAX, which are polydimethyldi($C_{10}$–$C_{20}$)alkylsiloxanes.

As a guide, the detergent compositions according to the invention generally have the following compositions:

(i) anionic surfactant(s): from 5 to 50% by weight, and preferably from 5 to 20% by weight, relative to the total weight of the detergent composition;

(ii) amphoteric surfactant(s) of the alkylbetaine type: from 1 to 50% by weight, and preferably from 1 to 20% by weight, relative to the total weight of the composition. Furthermore, the concentration of amphoteric surfactants is generally from 5 to 70% by weight, and preferably from 10 to 30% by weight, relative to the total weight of the anionic surfactant or surfactants present in the detergent formulation;

(iii) cationic guar gum(s): from 0.001% to 10% by weight, preferably from 0.005% to 5% by weight and still more preferably from 0.01% to 3% by weight relative to the total weight of the composition;

(iv) non-pre-emulsified insoluble silicone(s): from 0.05% to 10%, preferably from 0.1% to 5% and still more preferably from 0.2% to 3% relative to the total weight of the composition.

The vehicle or carrier of the detergent compositions according to the invention is preferably water or an aqueous-alcoholic solution of a lower alcohol such as ethanol, isopropanol or butanol.

The detergent compositions according to the invention have a final pH generally of between 3 and 9. Preferably, this pH is between 5 and 7. Adjustment of the pH to the desired value may be done in the traditional manner by adding a base (organic or inorganic) to the composition, for example aqueous ammonia or a primary, secondary or tertiary (poly) amine such as monoethanolamine, diethanolamine, triethanolamine, isopropanolamine or 1,3-propanediamine, or alternatively by adding an acid, preferably a carboxylic acid such as, for example, citric acid.

The detergent compositions according to the invention may naturally contain, in addition, all the standard adjuvants encountered in the field of shampoos, such as, for example, perfumes, preservatives, sequestering agents, thickeners, emollients, foam modifiers, colorants, pearlescent agents, hydrating agents, antidandruff or antiseborrhoeic agents, vitamins, sunscreen agents, suspending agents and the like.

Naturally, a person skilled in the art will take care to choose this/these possible supplementary compound(s) and/or the amounts thereof in such a way that the advantageous properties intrinsically associated with the quaternary combination (anionic surfactant+amphoteric surfactant of the alkylbetaine type+cationic guar gum+specific silicone) according to the invention are not, or are not substantially, impaired by the addition or additions envisaged.

These compositions may take the form of more or less thickened liquids, of creams or of gel, and they are mainly suitable for washing the hair, for hair care and/or for hair styling.

When the compositions according to the invention are employed as traditional shampoos, they are simply applied to wet hair, and the lather generated by massage or friction with the hands is then removed, after an optional period of exposure, by rinsing with water, it being possible for the operation to be repeated once or several times.

As stated above, the compositions according to the invention impart to the hair, after rinsing, a noteworthy treatment effect which manifests itself, in particular, in an ease of disentangling and of styling as well as a smoothness and softness which are markedly improved.

A subject of the invention is also a process for washing and conditioning keratinous fibres such as the hair, consisting in applying to the said fibres in the wet state an effective amount of a composition as defined above, and in then rising with water after an optional period of exposure.

A specific but in no way limiting example illustrating the invention will now be given.

EXAMPLE

A shampoo composition containing the following was produced:

| | |
|---|---|
| Sodium lauryl ether sulphate ($C_{12}$/$C_{14}$ in the ratio 70:30) containing 2.2 mol of ethylene oxide (AS = active substance) | 14 g AS |
| Cocoylbetaine in aqueous solution containing 32% of active substances (DEHYTON AE 30 from HENKEL) | 2.56 g AB |
| Cationic guar gum (*) | 0.05 g |
| Insoluble silicone (**) | 2.7 g |
| Mixture (47:53 by weight) of 1-hexadecyloxy-2-octadecanol and cetyl alcohol | 2.5 g |
| Coconut acid monoisopropanolamide | 1.6 g |
| Citric acid qs | pH 5 |
| Demineralized water qs | 100 g |

(*) guar gum modified with 2,3-epoxypropyltrimethylammonium chloride, sold under the name JAGUAR C13 S by the company RHONE POULENC
(**) polydimethylsiloxane sold under the name VISCOSIL 60,000 Cst by the company GENERAL ELECTRIC, used and introduced without further treatment into the composition to be prepared.

Shampooing is performed by applying approximately 12 g of the composition to previously wetted hair. The shampoo is worked to a lather and the hair is then rinsed copiously with water.

A panel of experts found that the compositions according to the invention impart to the hair, after rinsing, a noteworthy treatment effect which manifests itself, in particular, in an ease of disentangling and of styling as well as a noteworthy smoothness and softness of the hair.

What is claimed is:

1. A process for preparing a composition for detergent and conditioning hair-care comprising combining a washing base, a conditioning system, and a cosmetically acceptable medium;

wherein the washing base comprises at least one anionic surfactant and at least one $C_{10}$–$C_{14}$ alkylbetaine amphoteric surfactant; and wherein the conditioning system comprises at least one cationic guar gum and at least one insoluble silicone of viscosity less than or equal to 350,000 cSt, wherein said at least one insoluble silicone is present in the composition in a non-pre-emulsified form, and further wherein said at least one insoluble silicone is chosen from:
(i) polydialkylsiloxanes,
(ii) polydiarylsiloxanes, and
(iii) polyalkylarylsiloxanes.

2. A process for preparing a composition according to claim 1, wherein said at least one anionic surfactant is present in an amount ranging from 5 to 50% by weight relative to the total weight of the composition.

3. A process for preparing a composition according to claim 1, wherein said at least one amphoteric surfactant is present in an amount ranging from 1 to 50% by weight relative to the total weight of the composition.

4. A process for preparing a composition according to claim 3, wherein said at least one amphoteric surfactant is present in an amount ranging from 1 to 20% by weight relative to the total weight of the composition.

5. A process for preparing a composition according to claim 1, wherein said at least one amphoteric surfactant is present in an amount ranging from 5 to 70% by weight, relative to the total weight of said at least one anionic surfactant.

6. A process for preparing a composition according to claim 5, wherein said at least one amphoteric surfactant is present in an amount ranging from 10 to 30% by weight, relative to the total weight of said at least one anionic surfactant.

7. A process for preparing a composition according to claim 1, wherein said at least one amphoteric surfactant is cocoylbetaine.

8. A process for preparing a composition according to claim 1, wherein said at least one cationic guar gum is chosen from guar gums modified with hydroxypropyltrimethylammonium groups.

9. A process for preparing a composition according to claim 1, wherein said said at least one insoluble silicone is chosen from polydimethylsiloxanes containing terminal trimethylsilyl groups and polydimethylsiloxanes containing terminal hydroxydimethylsilyl groups.

10. A process for preparing a composition according to claim 1, wherein said at least one cationic guar gum is present in an amount ranging from 0.001% to 10% by weight relative to the total weight of the composition.

11. A process for preparing a composition according to claim 10, wherein said at least one cationic guar gum is present in an amount ranging from 0.005% to 5% relative to the total weight of the composition.

12. A process for preparing a composition according to claim 11, wherein said at least one cationic guar gum is present in an amount ranging from 0.01% to 3% relative to the total weight of the composition.

13. A process for preparing a composition according to claim 1, wherein said at least one insoluble silicone is present in an amount ranging from 0.05% to 10% by weight relative to the total weight of the composition.

14. A process for preparing a composition according to claim 13, wherein said at least one insoluble silicone is present in an amount ranging from 0.1% to 5% relative to the total weight of the composition.

15. A process for preparing a composition according to claim 14, wherein said at least one insoluble silicone is present in an amount ranging from 0.2% to 3%.

16. A process for preparing a composition according to claim 1, wherein the composition has a pH ranging from 3 to 9.

17. A process for preparing a composition according to claim 1, wherein the composition is an aqueous or aqueous-alcoholic composition.

18. A process for preparing a composition according to claim 1, wherein the washing base is free from surfactants other than anionic surfactants and $C_{10}$–$C_{14}$ alkylbetaine amphoteric surfactants.

19. A process for preparing a composition according to claim 1, wherein the conditioning system is free from cationic polymers other than cationic guar gums.

20. A process for washing and conditioning keratinous fibers comprising the steps of;
(a) applying to the fibers in the wet state a composition prepared according to claim 1 in an amount effective to wash and condition said fibers, and
(b) rinsing said fibers with water after a time effective for washing and conditioning said fibers.

21. A process according to claim 20, wherein said keratinous fibres are hair.

22. A process according to claim 21, wherein said hair is human hair.

23. A process for preparing a composition comprising combining a washing base, a conditioning system, and a cosmetically acceptable medium;

wherein the washing base comprises at least one anionic surfactant and at least one $C_{10}$–$C_{14}$ alkylbetaine amphoteric surfactant; and wherein the conditioning system comprises at least one cationic guar gum and at least one insoluble silicone of viscosity less than or equal to 350,000 cSt, wherein said at least one soluble silicone is present in the composition in a non-pre-emulsified form, and further wherein said at least one insoluble silicone is chosen from:
(i) polydialkylsiloxanes,
(ii) polydiarylsiloxanes, and
(iii) polyalkylarylsiloxanes.

* * * * *

UNITED STATES PATENT AND TRADEMARK OFFICE
CERTIFICATE OF CORRECTION

PATENT NO. : 6,551,970 B2
DATED : April 22, 2003
INVENTOR(S) : Sandrine Decoster et al.

It is certified that error appears in the above-identified patent and that said Letters Patent is hereby corrected as shown below:

Column 8,
Line 29, "of;" should read -- of: --.
Line 50, "soluble" should read -- insoluble --.

Signed and Sealed this

First Day of July, 2003

JAMES E. ROGAN
*Director of the United States Patent and Trademark Office*